United States Patent [19]

Dowrick

[11] 4,282,202
[45] Aug. 4, 1981

[54] INTRAMAMMARY COMPOSITIONS

[75] Inventor: John S. Dowrick, Littlehampton, England

[73] Assignee: Beecham Group Limited, England

[21] Appl. No.: 88,859

[22] Filed: Oct. 29, 1979

[30] Foreign Application Priority Data

Oct. 27, 1978 [GB] United Kingdom ............... 42336/78

[51] Int. Cl.$^3$ .......................... A61K 9/06; A61K 9/08; A61K 9/10; A61K 9/18
[52] U.S. Cl. ..................................... 424/23; 424/246; 424/271; 424/357
[58] Field of Search ................... 424/23, 357, 271, 246

[56] References Cited

U.S. PATENT DOCUMENTS

| | | | |
|---|---|---|---|
| 2,914,443 | 11/1959 | Lynch | 424/357 |
| 3,234,028 | 2/1966 | Dunham et al. | 424/357 |
| 3,250,680 | 5/1966 | Menkart et al. | 424/357 |
| 3,733,403 | 5/1973 | Chen | 424/357 |
| 3,912,806 | 10/1975 | Dowrick et al. | 424/16 |
| 3,923,969 | 12/1975 | Baukal et al. | 424/23 |
| 3,998,973 | 12/1976 | Carlson | 424/357 |
| 4,000,254 | 12/1976 | Gordon et al. | 424/23 |
| 4,064,230 | 12/1977 | Gordon et al. | 424/19 |
| 4,071,374 | 1/1978 | Minton | 424/357 |
| 4,145,429 | 3/1979 | Clarke | 424/357 |

FOREIGN PATENT DOCUMENTS 2635476  2/1977  Fed. Rep. of Germany ........... 424/271

OTHER PUBLICATIONS

Chemical Abstracts 73:48542m (1970) Czech Patent 132,788 6/15/69.
Chemical Abstracts 74:33288f (1971) [Malkin, L. et al. Khim. Tekhnd. Topl. Masel (1970) 15(9), 22-3].

*Primary Examiner*—Shep K. Rose
*Attorney, Agent, or Firm*—Jacobs & Jacobs

[57] ABSTRACT

The stability of an oily intramammary formulation containing a suspension of a solid clavulanic acid salt is improved by incorporation therein of molecular sieve powder.

5 Claims, No Drawings

INTRAMAMMARY COMPOSITIONS

This invention relates to intramammary compositions, to a process for their preparation, and to a method for their use.

U.K. Pat. No. 1508977 describes clavulanic acid, of formula (I):

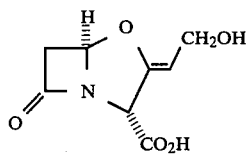

and its salts; and the use of such compounds as synergists for penicillins and cephalosporins.

Also described in this Patent is the use of such materials in the treatment of mastitis in cattle.

We have now discovered certain intramammary formulations not disclosed in U.K. Pat. No.: 1508977 which have very advantageous stability and shelf life.

Accordingly the present invention provides an intramammary composition comprising a suspension in an oily vehicle of a solid salt of clavulanic acid; and molecular sieve powder.

The salts of clavulanic acid used in the composition may be any of the solid salts described in U.K. Pat. No. 1508977 which are acceptable from a point of view of toxicity for intramammary administration.

It has been found that the compositions of this invention are especially effective when they contain an alkali, or alkaline earth metal, or t-butylamine [$NH_2C(CH_3)_3$] salt of clavulanic acid.

Most suitably the clavulanic acid salt is the sodium, potassium, calcium, magnesium or t-butylamine salt, preferably sodium or potassium.

Preferably the compositions of this invention will also contain a penicillin or cephalosporin.

Suitable penicillins and cephalosporins for use in these compositions include any of those set out in U.K. Pat. No. 1508977, more especially those well known in the art for mastitis therapy. Such penicillins include sodium amoxycillin, amoxycillin trihydrate, sodium ampicillin, ampicillin trihydrate, sodium cloxacillin, benzathine cloxacillin and sodium flucloxacillin.

It is believed that preferred compositions of this invention include sodium or potassium clavulanate; and sodium amoxycillin or amoxycillin trihydrate.

The weight ratio (as free acids) of the penicillin or cephalosporin to the clavulanic acid salt in such compositions is suitably 5:1 to 1:1, for example about 2:1 to 3:1.

In the compositions, the active ingredients (taken as free acids) will suitably represent 0.1 to 40%, more suitably 1 to 40% (w/w). Within these ranges particularly suitably values are 4 to 8%, 15 to 25% and 30 to 40%.

Molecular sieves are commercially available in powder form. Suitable molecular sieves for our use are for example crystalline sodium, potassium or calcium alumino-silicate, preferably the calcium alumino-silicate.

The molecular sieve powder will usually be present as 0.1 to 30%, more suitably 5 to 20% of the composition, by weight.

The oily vehicle may be a mineral oil, or a vegetable oil such as arachis oil, sesame oil, corn oil, cottonseed oil, soyabean oil, olive oil, or fractionated coconut oil.

The physical properties of the composition and the release rate of active ingredient may be varied by making an appropriate choice of oily vehicle and optional additives therefor. For example when a fast milk out is required for therapy of lactating cows, then an emulsifying agent may be included in the composition to hasten the mixing of the composition with the aqueous secretions in the udder; alternatively the base described in West Germany Offenlegungsschrift No. 26 35 476 may be used, namely fractionated coconut oil (the disclosure of this Offenlegungsschrift is incorporated herein by reference). If on the other hand slow release is required for the therapy of prophylaxis of dry cows, then suitably a more hydrophobic oil vehicle which has been more strongly gelled with a gelling agent, such as aluminium stearate, is used. Thickening agents such as Thixcin R and silica may also be included in the compositions if so desired, and when present will normally represent 0.1 to 8%, more suitably 1 to 5% of the composition by weight.

We have found that preferred compositions of the invention include those comprising a suspension in fractionated coconut oil of sodium amoxycillin or amoxycillin trihydrate; and sodium or potassium clavulanate; and molecular sieve powder; in which composition the weight ratio of amoxycillin to clavulanate salt (as free acids) is 5:1 to 1:1, the active ingredients (as free acids) represent 1 to 40% of the composition, and the molecular sieve represents 5 to 20% of the composition.

Usually it will be convenient to formulate the compositions of this invention as unit doses containing a therapeutically effective amount of the chosen active ingredient.

For example amoxycillin containing unit dose compositions suitably contain 100 to 1200 mg of amoxycillin (as free acid), for example 200 and 1000 mg.

Also unit dose compositions suitably contain 20 to 300 mg of clavulanic acid salt (as free acid), more suitably 25 to 100 mg.

The invention also provides a method of treatment or prophylaxis of mammary disorders in animals, which method comprises the intramammary administration of an effective amount of a composition of the invention.

For such administration, the chosen compositions will be filled into the tubes or syringe packs of the conventional type for intramammary administration, i.e. provided with a cannula nozzle for insertion into the teat to allow extrusion directly into the mammary gland via the streak canal.

A single dose of the composition will normally contain 1 to 10 gm., preferably 3 to 8 gm., of the composition.

Often a single dose of the composition of the invention will provide effective treatment of prophylaxis of the mammary disorder. However in lactating cow therapy it is common practice to repeat the dose at least once (preferably three times), each dosing taking place after milking.

The compositions of the invention may be prepared by mixing the active ingredient and the molecular sieve with the oily vehicle.

This process may suitably be carried out stepwise as follows:

(a) if a gelled or thickened base is to be used, the oil is heated, the gelling or thickening agent mixed in, and the oil then allowed to cool;

(b) the powdered active ingredient and molecular sieve is mixed into the base with stirring; and (c) high shear mixing equipment is used to produce a fine, homogeneous dispersion.

The following Examples illustrate the invention.

EXAMPLE 1

|  | gms |
| --- | --- |
| Sodium Amoxycillin | 33.3 (as free acid) |
| Potassium Clavulanate | 16.7 (as free acid) |
| Thixcin R | 3.75 |
| Molecular Sieve (5Å) | 50 |
| Miglyol 812    to | 500 gms |

This composition was prepared as follows:

3.75 gms of Thixcin R were dissolved in dried Miglyol 812 by heating to about 60° C. and stirring, then allowed to cool. 50 gms of re-activated molecular sieve (calcium alumino-silicate) were incorporated by high shear stirring.

16.7 gms (free acid) of potassium clavulanate, and 33.3 gms (free acid) of sodium amoxycillin (pre-dried over phosphorous pentoxide) were incorporated into the base by high shear stirring. The weight of the suspension was adjusted to 500 gms by the addition of Miglyol 812.

The suspension was filled as 3 gm doses into intramammary syringes.

[Miglyol 812 has the approximate composition:
Triglyceride of caproic acid: 3% max.
Triglyceride of caprylic acid: 50–65%
Triglyceride of capric acid: 30–45%
Triglyceride of lauric acid: 5% max.
and is available from Dynamit-Nobel U.K., Slough, Bucks, England.

Thixcin R is 12-hydroxystearin.

Molecular Sieve 5Å is commercially available from Union Carbide, and is known as calcium alumino-silicate.]

EXAMPLE 2

| Amoxycillin Trihydrate | 33.3 (as free acid) |
| --- | --- |
| Potassium Clavulanate | 16.7 (as free acid) |
| Thixcin R | 3.75 |
| Molecular Sieve (5Å) | 50 |
| Miglyol 812    to | 500 gms |

This composition was prepared as follows:

3.75 gms of Thixcin R were dissolved in dried Miglyol 812 by heating to about 60° C. and stirring, then allowed to cool. 50 gms of re-activated molecular sieve (calcium alumino-silicate) was incorporated by high shear stirring.

16.7 gms (free acid) of potassium clavulanate and 33.3 gms (free acid) of amoxycillin trihydrate (pre-dried over silica gel) were incorporated into the base by high shear stirring. The weight of the suspension was adjusted to 500 gms by the addition of Miglyol 812.

The suspension was filled as 3 gm doses into intramammary syringes.

EXAMPLE 3

|  | gms |
| --- | --- |
| Sodium Amoxycillin | 20 (as free acid) |
| Potassium Clavulanate | 10 (as free acid) |
| Thixcin R | 2.25 |
| Molecular Sieve (5Å) | 50 |
| Miglyol 812    to | 300 gms |

This composition was prepared as follows:

2.25 gms of Thixcin R were dissolved in dried Miglyol 812 by heating to about 60° C. and stirring, then allowed to cool. 50 gms of re-activated molecular sieve (calcium alumino-silicate) were incorporated by high shear stirring. 10 gms (free acid) of potassium clavulanate, and 20 gms (free acid) of sodium amoxycillin (pre-dried over silica gel) were also incorporated into the base by high shear stirring. The weight of the suspension was adjusted to 300 gms by the addition of Miglyol 812.

The suspension was filled as 3 gm doses into intramammary syringes, (dried at 50° C. for 72 hours).

EXAMPLE 4

|  | gm |
| --- | --- |
| Sodium Ampicillin | 33.3 as free acid |
| Sodium Clavulanate | 16.7 as free acid |
| Thixcin | 3.75 |
| Molecular Sieve (5Å) | 50.0 |
| Miglyol 812    to | 500.0 |

3.75 g of Thixcin R were incorporated into the Miglyol 812 at a temperature of 55° C. using a high shear silverson mixer. After cooling to room temperature, 50.0 g of molecular sieve (reactivated) and the appropriate amount of penicillin and clavulanic acid salt were incorporated into the base using the silverson high shear mixer. The resulting suspension was filled into intramammary syringes in 3 g doses.

The suspension was creamy coloured.

EXAMPLE 5

|  | gm |
| --- | --- |
| Sodium Cloxacillin | 33.3 as free acid |
| Sodium Clavulanate | 16.7 as free acid |
| Thixcin R | 3.75 |
| Molecular Sieve (5Å) | 50.0 |
| Miglyol 812    to | 500.0 |

The method used was analogous to that for Example 4, resulting in a creamy suspension.

EXAMPLE 6

|  | gm |
| --- | --- |
| Amoxicillin Sodium | 33.3 as free acid |
| Sodium Clavulanate | 16.7 as free acid |
| Thixcin R | 3.75 |
| Molecular Sieve (5Å) | 50.0 |
| Miglyol 812    to | 500.0 |

The method used was analogous to that of Example 4, resulting in a pinkish suspension.

EXAMPLE 7

|  | gm |
|---|---|
| Flucloxacillin | 33.3 as free acid |
| T-Butylaminoclavulanate | 16.7 as free acid |
| Thixcin R | 3.75 |
| Molecular Sieve (5Å) | 50.0 |
| Miglyol 812 to | 500.0 |

The method used was analogous to that for Example 4, resulting in a pinkish suspension.

EXAMPLE 8

|  | gm |
|---|---|
| Sodium Ampicillin | 33.3 as free acid |
| T-Butylaminoclavulanate | 16.7 as free acid |
| Thixcin R | 3.75 |
| Molecular Sieve (5Å) | 50.0 |
| Miglyol 812 to | 500.0 |

The method used was analogous to that of Example 4, resulting in a cream coloured suspension being formed.

EXAMPLE 9

|  | gm |
|---|---|
| Amoxycillin Trihydrate | 33.3 as free acid |
| T-Butylaminoclavulanate | 16.7 as free acid |
| Thixcin R | 3.75 |
| Molecular Sieve (5Å) | 50.0 |
| Miglyol 812 to | 500.0 |

The method used was analogous to that of Example 4, resulting in a pale yellow suspension.

EXAMPLE 10

|  | gm |
|---|---|
| Sodium Flucloxacillin | 33.3 as free acid |
| Sodium Clavulanate | 16.4 as free acid |
| Thixcin R | 3.75 |
| Molecular Sieve (5Å) | 50.0 |
| Miglyol 812 to | 500.0 |

The method used was analogous to that for Example 4, resulting in a pink coloured suspension.

What we claim is:

1. A liquid veterinary composition adapted for intramammary administration comprising a suspension of a powered solid pharmaceutically acceptable alkali metal, alkaline earth metal or amine salt of clavulanic acid in an amount of from 1 to 40% by weight of said composition calculated on the basis of the equivalent weight of free clavulanic acid, and from 5 to 20% by weight of a powdered solid molecular sieve in a pharmaceutically acceptable oil carrier.

2. A composition according to claim 1 also containing a penicillin or cephalosporin.

3. A composition according to claim 2 wherein the solid salt of clavulanic acid is the sodium potassium, calcium, magnesium or t-butylamine salt.

4. A composition according to claim 2 wherein the penicillin is sodium amoxycillin, amoxycillin trihydrate, sodium ampicillin, ampicillin trihydrate, sodium cloxacillin, benzathine cloxacillin or sodium flucloxacillin.

5. An intramammary composition comprising a suspension in fractioned coconut oil of sodium amoxycillin or amoxycillin trihydrate; sodium or potassium clavulanate; and molecular sieve powder; in which composition the weight ratio of amoxycillin to clavulanate salt (as free acids) is from 5:1 to 1:1, the active ingredients (as free acids) is from 1 to 40% of the composition, and the molecular sieve is from 5 to 20% of the composition.

* * * * *